(12) United States Patent
Kuo et al.

(10) Patent No.: US 8,292,819 B2
(45) Date of Patent: Oct. 23, 2012

(54) SLEEP ANALYSIS SYSTEM AND METHOD FOR ANALYZING SLEEP THEREOF

(75) Inventors: Bo-Jau Kuo, Taipei (TW); Ching-Hsiu Yang, Taipei (TW)

(73) Assignee: National Yang-Ming University, Taipei (JP)

( * ) Notice: Subject to any disclaimer, the term of this patent is extended or adjusted under 35 U.S.C. 154(b) by 513 days.

(21) Appl. No.: 12/408,811

(22) Filed: Mar. 23, 2009

(65) Prior Publication Data

US 2010/0125215 A1 May 20, 2010

(30) Foreign Application Priority Data

Nov. 17, 2008 (TW) .............................. 97144335 A

(51) Int. Cl.
*A61B 5/00* (2006.01)
*A61B 5/02* (2006.01)
*A61B 5/04* (2006.01)

(52) U.S. Cl. ........ 600/483; 600/301; 600/509; 600/513; 600/534

(58) Field of Classification Search .................. 600/483, 600/509, 513, 534, 301
See application file for complete search history.

(56) References Cited

U.S. PATENT DOCUMENTS

| 6,605,038 B1* | 8/2003 | Teller et al. .................. 600/300 |
| 2005/0190065 A1* | 9/2005 | Ronnholm ..................... 340/575 |
| 2005/0209511 A1* | 9/2005 | Heruth et al. ................. 600/301 |

* cited by examiner

*Primary Examiner* — Nicole F Lavert
(74) *Attorney, Agent, or Firm* — Muncy, Geissler, Olds & Lowe, PLLC

(57) ABSTRACT

The invention provides a sleep analysis system and a method for analysis thereof. The sleep analysis system includes an analysis device and a sleep sensing apparatus. The sleep sensing apparatus includes an ECG signal collector, a multi-axial accelerometer, a wireless transmitting unit, and a control unit. The ECG signal collector is used for collecting an ECG signal associated with a subject. The multi-axial accelerometer is used for detecting a multi-axial accelerometer signal associated with the subject. The control unit controls the wireless transmitting unit to transmit the ECG signal and the multi-axial accelerometer signal to the analysis device for analyzing sleep of the subject.

7 Claims, 4 Drawing Sheets

SLEEP ANALYSIS SYSTEM AND METHOD FOR ANALYZING SLEEP THEREOF

BACKGROUND OF THE INVENTION

1. Field of the Invention

The invention relates to a sleep analysis technology; more particularly, this invention relates to a sleep analysis system, a sleep sensing apparatus, and a method for analyzing sleep thereof.

2. Description of the Related Art

In medicine, it takes a long period of observation to further understand the statuses of patients. Sleep medicine has made great progress in the last five years, including apnea and some other chronic diseases related to sleep have been paid more attention to. Some medical research has also shown that sleep problems may be one of the causes of hypertension. The amount of relevant research and clinical examinations on sleep has also grown significantly. The implementation of sleep-related research is one of the focuses in the future development of medicine. However, in the present medicine, due to the slow progress of the relevant research on sleep, sleep has become a missing issue in the clinical medicine.

At present, the commonly used sleep examinations or analysis can be divided into two extremes. One measuring method is implemented with a conventional polysomnography. The subjects have to be attached with many electrodes on their bodies, and then these electrodes are connected to an amplifier via conducting wires to implement analog-digital converting afterwards. It is very inconvenient since the subjects are covered by many wires and are connected to a socket via power wires of a host, so that subjects' activity is greatly limited, even going to washroom is made inconvenient.

The other measuring method is extremely simple since the subjects only need to wear a watch (e.g. an active watch) to record data for a period of time in a simple way, and calculates the resulting parameters for each time to show sleep analysis. Although the application is easy, the accuracy is insufficient. Even though the analysis results deserve some attention, they still can not be compared with the conventional sleep analysis method.

BRIEF SUMMARY OF THE INVENTION

An object of this invention is to provide a sleep analysis system, a sleep sensing apparatus, and a method for analyzing sleep thereof to improve the disadvantages of current technology.

This invention is characterized by providing a sleep sensing apparatus for attachment to a subject to work with an analysis device. The sleep sensing apparatus includes an electrocardiogram (ECG) signal collector, a multi-axial accelerometer, a wireless transmitting unit, and a control unit. The ECG signal collector is used for collecting the ECG signals associated with the subjects. The multi-axial accelerometer is used for detecting a multi-axial accelerometer signal associated with the subjects. The control unit is coupled to the ECG signal collector, the multi-axial accelerometer, and the wireless transmitting unit to control the wireless transmitting unit to transmit the ECG signals and the multi-axial accelerometer signals to the analysis device.

This invention is further characterized by providing a sleep analysis system used for analyzing the sleep status of a subject. The sleep analysis method includes: an analysis device and a sleep sensing apparatus. The sleep sensing apparatus is connected to the analysis device wirelessly, and the sleep sensing device includes an ECG signal collector, a multi-axial accelerometer, a wireless transmitting unit, and a control unit. The ECG signal collector is used for collecting ECG signals associated with the subjects. The multi-axial accelerometer is used for detecting multi-axial accelerometer signals associated with the subjects. The control unit is coupled to the ECG signal collector, the multi-axial accelerometer, and the wireless transmitting unit to control the wireless transmitting unit to transmit the ECG signals and the multi-axial accelerometer signals to the analysis device.

This invention is yet further characterized by providing a method for analyzing sleep status of a subject. The method for analyzing sleep includes: collecting ECG signals of a subject to obtain detected ECG signals; detecting the activity of a subject to obtain multi-axial accelerometer signals; performing the first operation using multi-axial accelerometer signals to analyze the sleep status of a subject; performing the second operation using the ECG signals to analyze a sleep mode of the subjects.

The advantages of this invention are that the conventional electromyography (EMG) signals are replaced by activity signals to determine that the subjects are awake. Furthermore, the troublesome measuring and judging methods of electroencephalography (EEG) detection are replaced by HRV analysis to distinguish REM and NREM, so as to provide a simple and accurate sleep analysis device.

These and other features, aspects, and advantages of the present invention will become better understood with regard to the following description, appended claims, and appended drawings.

DETAILED DESCRIPTION OF THE EMBODIMENTS

Figure 1:
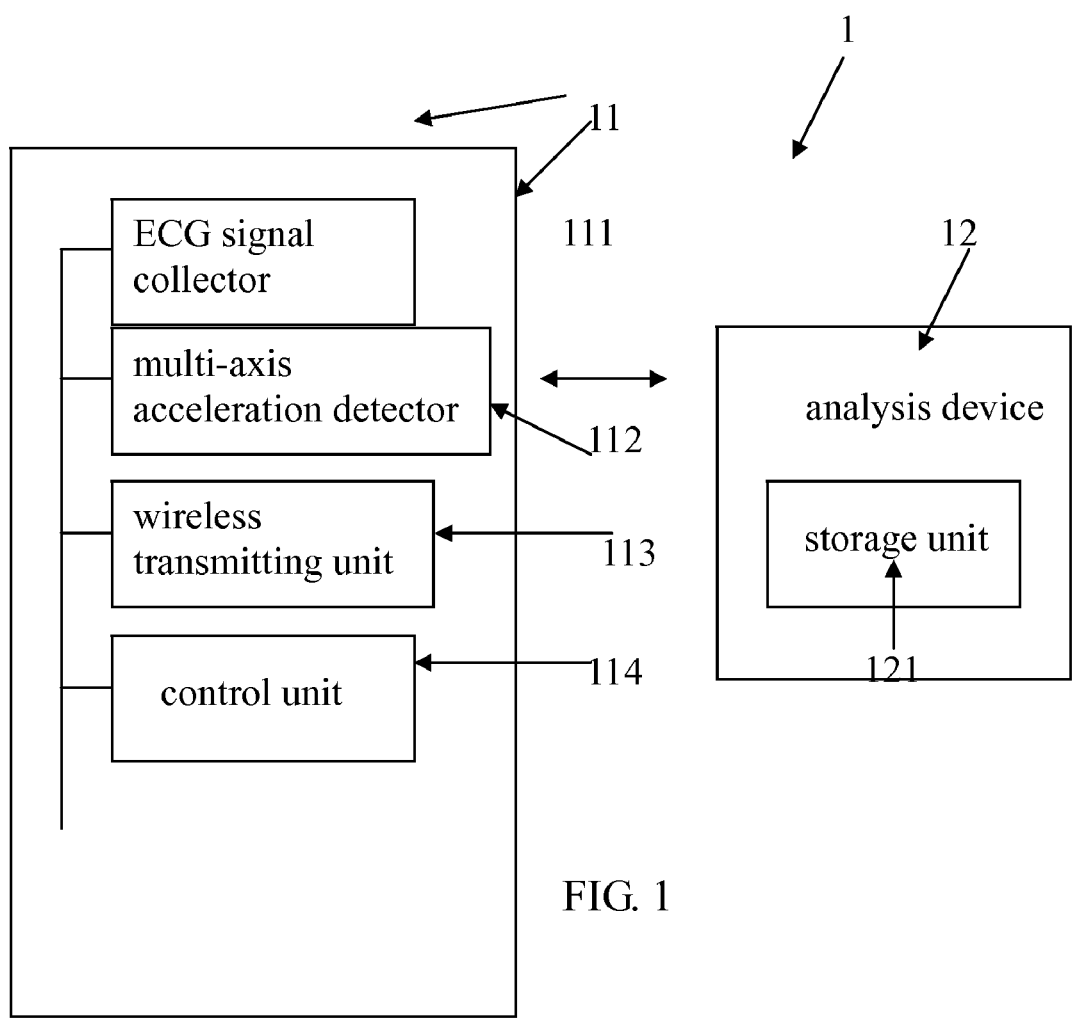
FIG. 1 is a schematically illustrates an embodiment of the sleep analysis system according to this invention.

FIG. 1 schematically illustrates an embodiment of a sleep analysis system according to this invention. The sleep analysis system 1 of this embodiment includes a sleep sensing apparatus 11 and an analyzing device 12; wherein the sleep sensing apparatus 11 further includes an ECG signal collector 111, a multi-axial accelerometer 112, a wireless transmitting unit 113, and a control unit 114. The analyzing device 12 includes a storage unit 121.

The sleep sensing apparatus 11 above is provided for working with the analysis device 12. In this embodiment, the sleep sensing apparatus 11 can be integrated into a watch, a necklace, or an accessory to be worn on subjects. Therefore, it can be easily worn and will not affect activities of a subject. For example, the sleep sensing apparatus 11 can be stuck to or positioned against the chest of the subject. In this embodiment, the analysis device 12 can be a computer.

The control unit 114 above is coupled to the ECG signal collector 111, the multi-axial accelerometer 112, and the wireless transmitting unit 113. The control unit 114 communicates with the analysis device 12 wirelessly.

The ECG signal collector 111 above is used for collecting the ECG signals associated with the subjects. In this embodiment, the ECG signal collector 111 adopts diode input method. However, this invention is not limited thereto.

In this embodiment, the multi-axial accelerometer 112 is a tri-axial accelerometer for detecting multi-axial accelerometer signals associated with the subject.

The control unit 114 above receives the ECG signals and the multi-axial accelerometer signals from the ECG signal collector 111 and the multi-axial accelerometer 112, respectively. Furthermore, the control unit 114 processes the ECG signals and the multi-axial accelerometer signals by performing filtering, amplifying, analog-digital converting, digital signal processing and so on. The control unit 114 also controls the wireless transmitting unit 113 to transmit the processed ECG signals and multi-axial accelerometer signals to the analysis device 12, and therefore the sleep of the subjects can be analyzed.

In this embodiment, the analysis device 12 first identifies heartbeats according to the ECG signals provided by the ECG signal collector 111. The digitized ECG signals and the pulse signals are processed with the following methods:

Identify the peak in each heartbeat oscillation using a peak detecting procedure to represent each heartbeat From each representative peak, the analysis device 12 can measure the height, duration and other parameters thereof, and obtain the mean value and the standard deviation of each parameter to be a standard template. Then, the parameter values of each heartbeat are compared with those of this standard template. If the parameter values of a certain heartbeat fall outside three of the standard deviations of the standard template, the heartbeat may be regarded as a noise thus to be filtered.

Next, the analysis device 12 measures the length of the interval between two adjacent heartbeat peaks to be the period of the heartbeat. All of the mean values and the standard deviations of all the heartbeat periods are obtained, and thus all the heartbeat periods confirmation can be implemented. If the parameter values of a certain heartbeat period fall outside three of the standard deviations of the template, it may also be regarded as a noise or unstable signals thus to be filtered. The heartbeat periods that pass the identification procedure may be analyzed by further analysis method.

The analysis methods of the analysis device 12 provided by this embodiment 12 will be briefly described below.

The ECG signal collector 111 of this embodiment can detect and quantify the autonomic nerve function of subjects' hearts through slight variations (i.e. heart rate variability (HRV)), when the subjects are taking a rest. That is, the ECG signal collected by the ECG signal collector 111 of this embodiment can be used to analyze or diagnose the autonomic nerve function of the subjects.

Generally speaking, the operation of HRV can be performed in regard to time domain, such as standard deviation of normal to normal intervals (SDNN), or to frequency domain (spectrum analysis).

In this embodiment, the description about the analysis device 12 performing the spectrum analysis is stated below. The analysis device 12 implements a sample-and-hold procedure to maintain time continuation of the accepted heartbeat periods at 7.11 Hz. The spectrum analysis is implemented using Fourier method. First straight-drift of the signals is eliminated to avoid interference from low frequency bands. Also, Hamming algorithm is adopted to prevent leakage of each frequency component from other spectrums. Next power density spectrum is obtained using fast fourier transform by taking data for 288 seconds (2048 points totally), and the effects caused by sampling and Hamming algorithm are offset.

Power of two of frequency bands in the power density spectrum of HRV are quantified using the integration method, including power of low frequency (LF, 0.04-0.15 Hz) and high frequency (HF, 0.15-0.4 Hz). Meanwhile, the quantified total power (TP) and ratio of the low frequency to the high frequency (LF/HF ratio) are also obtained. The parameters can be distributed normally by logarithmic transform.

During the spectrum analysis, slight variations in HRV mainly include an HF value and an LF value. In which, the HF component synchronizes with the breathing signals of the subjects, and therefore it is also called breathing component. The LF component may be associated with motion of blood vessel or baroreflex.

However, SDNN and the high frequency component or the total power of HRV can indicate pneumogastric nerve (parasympathetic nerve) functions. The LF/HF ratio or the percentage of LF that occupies the sum of LF and HF (LF %) can reflect sympathetic nerve activity of the heart, while the case for the percentage of HF that occupies the sum of LF and HF (HF %) is completely opposite.

Further, sleep modes of the subject may include the first sleep mode and the second sleep mode. Here the so-called first sleep mode refers to the NREM of awake status and asleep status. The second sleep mode is rapid eye movement (REM). However, both the first sleep mode and the second sleep mode are associated with the heart rate (HR), the aforementioned high frequency component, and the aforementioned low frequency component.

For example, when a subjects is awake, the HR and the LF/HF value indicating the sympathetic nerve activity may be higher (the highest), while the HF value indicating the parasympathetic nerve activity is lower (the lowest). When the subject is in the first sleep mode (NREM sleep), the HR and the LF/HF ratio may decrease (the lowest) and the HF may increase (the highest). When the subject is in the second sleep mode (REM sleep), the HR and the LF/HF ratio may increase and the HF may decrease and approach the value that when the subject is going to wake up while not completely awake; wherein, the LF/HF ratio can distinguish between NREM sleep and REM sleep most clearly, and it is also an important judging criterion in this embodiment. After the analysis device 12 of this embodiment receives the processed ECG signals, the analysis device 12 can identify the low frequency component, the high frequency component, the HR, the LF/HF ratio, and other associated parameters from the ECG signals thus to further analyze sleep.

The analysis device 12 of this embodiment analyzes sleep using not only the multi-axial accelerometer signals but also the ECG signals.

The sleep sensing apparatus 11 of the embodiment can be worn anywhere by the subjects, such that the implementation of sleep-related measurement is simplified. Further, the multi-axial accelerometer 112 of the sleep sensing apparatus 11 can be used to detect activity of the subject thus to determine whether the subject is in awake status or sleep.

Figure 2:
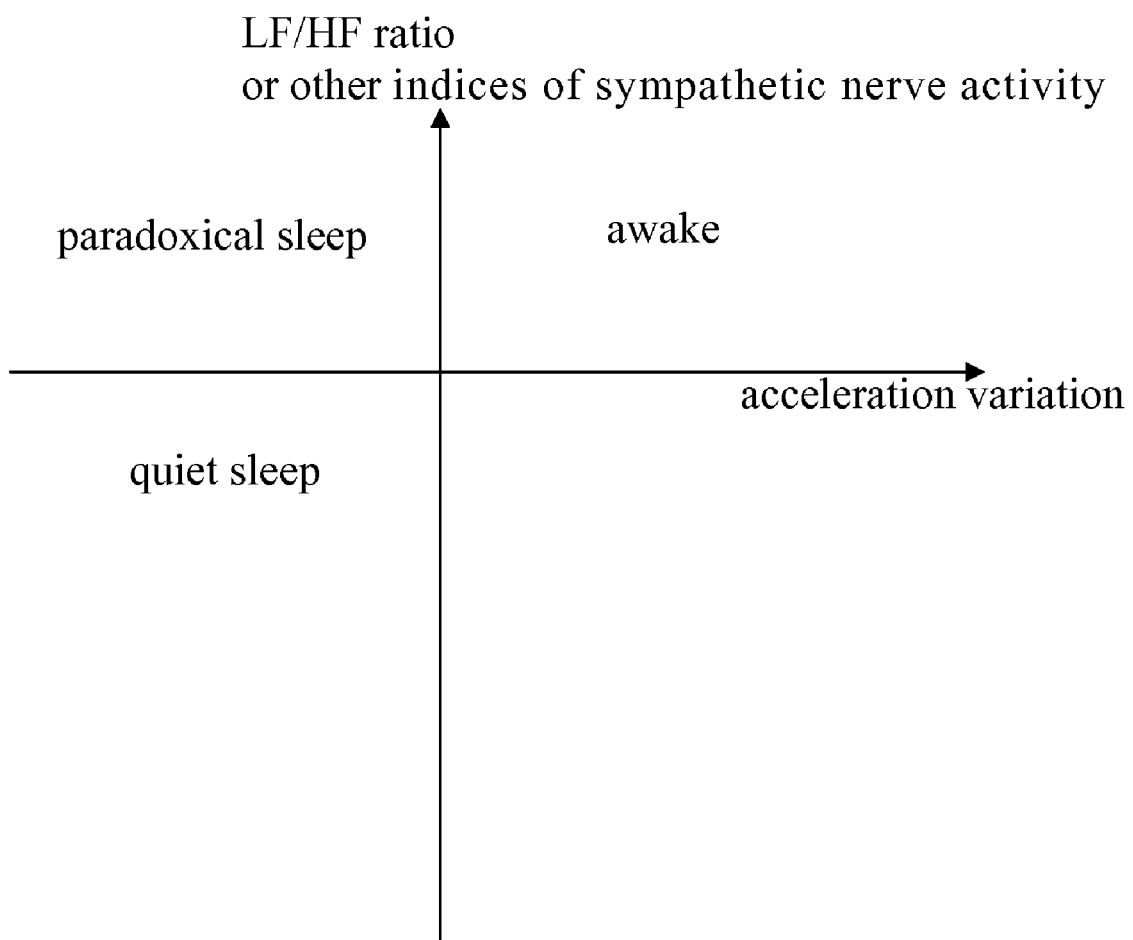
FIG. 2 is a coordinate diagram showing the relations between the acceleration variation and the index of sympathetic nerve activity according to an embodiment of this invention.

FIG. 2 is a coordinate diagram showing the relations between the acceleration variation and the index of sympathetic nerve activity of a preferred embodiment of this invention. The horizontal axis of the coordinate indicates acceleration variation (Act), and the vertical axis indicates the LF/HF ratio or other indices of sympathetic nerve activity. The diagram shows four quadrants including awake (AW), the REM sleep or paradoxical sleep (PS), and the NREM sleep or quiet sleep (QS).

In this embodiment, the analysis device 12 obtains the acceleration variation with following methods. The tri-axial accelerometer detects three components, including x-axis acceleration, y-axis acceleration, and z-axis acceleration (the acceleration at each time point); the signals of which are sampled 62 points per second, and the simultaneous three points respectively in the three components are obtained using a formula $A=\sqrt{x^2+y^2+z^2}$ where A represents total acceleration at each time point (the unit is G). The value of A integrates energy of the three components in the x-axis, the y-axis, and the z-axis, and therefore it may vary accordingly. Then the amplitude variation is obtained using root mean square (RMS) method at a certain interval (about one second), and it is the acceleration variation (Act) indicating activity.

Figure 3:
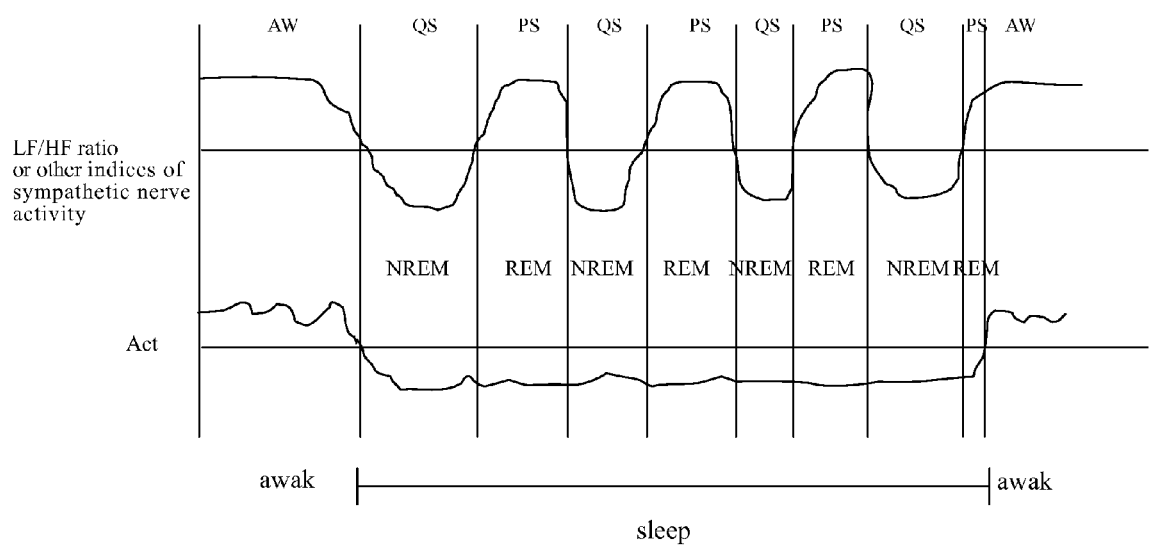
FIG. 3 schematically illustrates the relation between an acceleration variation and a sleep status or an awake status according to an embodiment of the invention.

FIG. 3 schematically illustrates the relation between an acceleration variation and a sleep status or an awake status of a preferred embodiment of the invention. In FIG. 3, it can be clearly seen that the tri-axis acceleration and the obtained activity parameter (acceleration variation) are even more sensitive than an EMG signal often used by the conventional determination criterion. Further, the cutoff point between the sleep status and the awake status can be easily identified by naked eyes. The analysis device 12 can generate a histogram by analyzing the acceleration variations for all the recorded data, thus identifying activity distribution in the awake and sleep statuses. The cutoff point between the two status is identified as a threshold, and a horizontal line is drawn accordingly. The points below that contacting the horizontal line are defined as the sleep status, while the points above that contacting the horizontal line are defined as the awake status.

To sum up, in FIG. 2 and FIG. 3, the obtained acceleration variations according to the tri-axis acceleration in the sleep status are quite different from those of awake status. Therefore, the analysis device 12 can automatically identify the intersection of the normal distribution of the acceleration variations in the awake and sleep statuses to be the threshold value. The variations greater than the threshold value are identified as awake status, while the variations less than the threshold value are identified as sleep status. Further, the analysis device 12 can also obtain time points of sleep and awake. The body of a subject seldom moves in the sleep status, and therefore steady ECG signals can be obtained. Then the analysis device 12 can further obtain HRV using the ECG signals. In which, the LF/HF ratio, other indices of sympathetic nerve activity, or value distribution after mathematical calculations can be used for distinguishing the NREM sleep and the REM sleep, and the HR and the HF can be used to assist in the distinguishing process.

Figure 4:
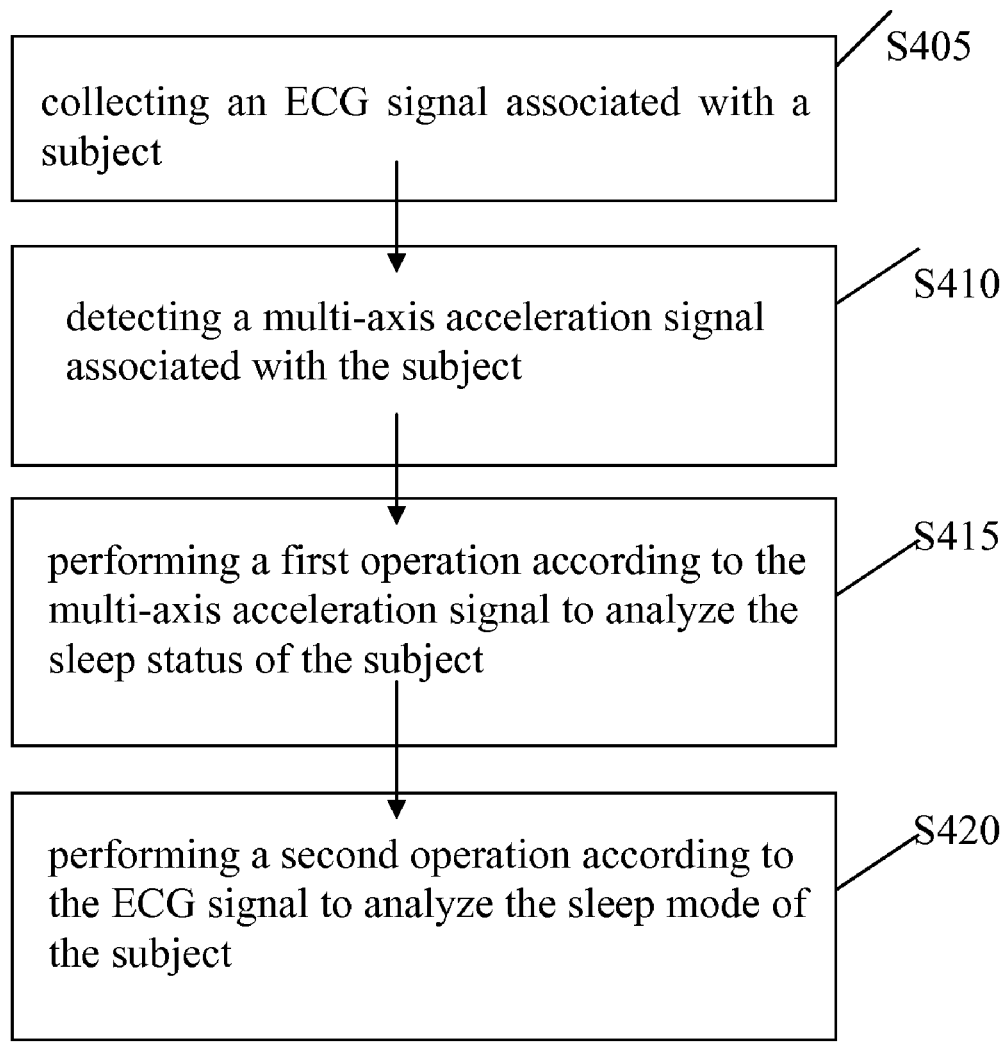
FIG. 4 is a flowchart of an embodiment according to the invention.

FIG. 4 is a flowchart of a preferred embodiment of this invention. Please refer to FIG. 1, FIG. 2, FIG. 3, and FIG. 4 for its description.

In step S405, the ECG signal collector 111 of the sleep sensing apparatus 11 collects the ECG signals associated with the subjects to implement HRV analysis. The control unit 114 of the sleep sensing apparatus 11 can control the wireless transmitting unit 113 to transmit the ECG signals to the analysis device 12 for processing. The storage unit 121 in the analysis device 12 can store the analysis results immediately.

In step S410, the multi-axial accelerometer 112 of the sleep sensing apparatus 11 detects the multi-axial accelerometer signal associated with the subjects. The control unit 114 of the sleep sensing apparatus 11 can control the wireless transmitting unit 113 to transmit the multi-axial accelerometer signals to the analysis device 12 for calculation of the acceleration variation and analysis. The storage unit 121 in the analysis device 12 can store the analysis results immediately.

What needs to point out is that the order of step S405 and step S410 can be changed and this invention is not limited to the aforementioned implementation order.

In step S415, the analysis device 12 performs a first operation using the multi-axial accelerometer signals to analyze the sleep status of a subject (asleep or awak). That is, the analysis device 12 of this embodiment can determine whether the subject is on a sleep status or an awak status according to the acceleration variation.

In step S420, the analysis device 12 performs a second operation according to the ECG signal to analyze the sleep mode of the subject (REM sleep or NREM sleep). That is, the analysis device 12 performs the second operation according to the ECG signals to analyze HRV thus to obtain an HRV analysis result. The HRV analysis result can be temporally stored in the storage unit 121. The analysis device 12 can determine whether the subject is in a first sleep mode or a second sleep mode according to the HRV analysis result. In which, the first sleep mode includes the NREM sleep and the quiet sleep, and the second sleep mode includes the REM sleep and the paradoxical sleep.

Further, the HRV analysis result includes a low frequency vale and a high frequency value. The analysis device 12 determines the first sleep mode and the second sleep mode according to a ratio of the low frequency component to the high frequency component.

What needs to point out is that the order of step S415 and step S420 can be changed. This invention is not limited to the aforementioned implementation order.

To sum up, the analysis device 12 of this embodiment uses HRV, instead of EEG, to be the distinguishing criterion of the first sleep mode (NREM sleep) and the seconding sleep mode (REM sleep). Further, the analysis device 12 uses the detected acceleration variation from the multi-axial accelerometer 112, instead of EMG used in the prior art, to determine whether the subject is in the awak status or the sleep status. A simple and accurate sleep analysis device can be obtained thus.

Although the present invention has been described in considerable detail with reference to certain preferred embodiments thereof, the disclosure is not for limiting the scope of the invention. Any ordinary skilled person in the art may make various modifications and changes without departing from the scope and spirit of the invention. Therefore, the scope of the appended claims should not be limited to the description of the preferred embodiments described above.

What is claimed is:

1. A sleep sensing apparatus for attachment to a subject and cooperating with an analysis device, the sleep sensing apparatus comprising:
   an electrocardiogram (ECG) signal collector for collecting an ECG signal associated with the subject;
   a multi-axial accelerometer for detecting a multi-axial accelerometer signal associated with the subject;
   a wireless transmitting unit; and
   a control unit coupled to the ECG signal collector, the multi-axial accelerometer, and the wireless transmitting unit, to control the wireless transmitting unit to transmit the ECG signal and the multi-axial accelerometer signal to the analysis device,
   wherein the analysis device performs a first operation using the multi-axial accelerometer signal to obtain an acceleration variation, and the analysis device determines whether the subject is on a sleep status or an awake status according to the acceleration variation, and the analysis device performs a second operation using the ECG signal to analyze heart rate variability (HRV) thus to obtain an HRV analysis result which comprises a low frequency component and a high frequency component, and the analysis device determines whether the subject is in a first sleep mode or a second sleep mode according to a ratio of the low frequency component to the high frequency component.

2. The sleep sensing apparatus according to claim 1, wherein the sleep sensing apparatus is integrated in a watch, a necklace, or an accessory.

3. The sleep sensing apparatus according to claim 1, wherein the first sleep mode comprises non-rapid eye movement (NREM) sleep and quiet sleep.

4. The sleep sensing apparatus according to claim 1, wherein the second sleep mode comprises rapid eye movement (REM) sleep and paradoxical sleep.

5. A sleep analysis system for analyzing sleep of a subject, the sleep analysis system comprising:

an analysis device; and a sleep sensing apparatus wirelessly connected with the analysis device, the sleep sensing apparatus including:

an ECG signal collector used for collecting an ECG signal associated with the subject;

a multi-axial accelerometer used for detecting a multi-axial accelerometer signal associated with the subject;

a wireless transmitting unit; and a control unit coupled to the ECG signal collector, the multi-axial accelerometer, and the wireless transmitting unit to control the wireless transmitting unit to transmit the ECG signal and the multi-axial accelerometer signal to the analysis device, wherein the analysis device performs a first operation using the multi-axial accelerometer signal to obtain an acceleration variation, and the analysis device determines whether the subject is on asleep status or awake state according to the acceleration variation, and the analysis device performs a second operation using the ECG signal to analyze HRV thus to obtain an HRV analysis result which comprises a low frequency component and a high frequency component, and the analysis device determines whether the subject is in a first sleep mode or a second sleep mode according to a ratio of the low frequency component to the high frequency component.

6. The sleep analysis system according to claim 5, wherein the first sleep mode comprises NREM 5 sleep and quiet sleep.

7. The sleep analysis system according to claim 5, wherein the second sleep mode comprises REM sleep and paradoxical sleep.

* * * * *